US007554440B2

(12) United States Patent
Kadaba

(10) Patent No.: US 7,554,440 B2
(45) Date of Patent: Jun. 30, 2009

(54) SYSTEMS AND METHODS FOR MONITORING TRAVEL CONDITIONS

(75) Inventor: Nagesh Kadaba, Roswell, GA (US)

(73) Assignee: United Parcel Service of America, Inc., Atlanta, GA (US)

( * ) Notice: Subject to any disclaimer, the term of this patent is extended or adjusted under 35 U.S.C. 154(b) by 166 days.

(21) Appl. No.: 11/459,741

(22) Filed: Jul. 25, 2006

(65) Prior Publication Data

US 2008/0024323 A1    Jan. 31, 2008

(51) Int. Cl.
*G08B 1/08* (2006.01)
(52) U.S. Cl. .......................... 340/539.22; 340/539.26; 340/539.28; 340/905; 455/67.11
(58) Field of Classification Search ............... 340/905, 340/601, 995.12, 539.22–539.28; 455/67.11
See application file for complete search history.

(56) References Cited

U.S. PATENT DOCUMENTS

| 3,822,049 | A |  | 7/1974 | Saunders |
| 4,113,217 | A |  | 9/1978 | O'Connell |
| 4,124,815 | A |  | 11/1978 | Stoschek |
| 4,977,399 | A |  | 12/1990 | Price et al. |
| 5,095,500 | A |  | 3/1992 | Tayloe et al. |
| 5,398,276 | A |  | 3/1995 | Lemke et al. |
| 5,481,588 | A |  | 1/1996 | Rickli et al. |
| 5,561,839 | A |  | 10/1996 | Österberg et al. |
| 5,752,164 | A |  | 5/1998 | Jones |
| 5,818,356 | A |  | 10/1998 | Schuessler |
| 5,867,785 | A |  | 2/1999 | Averbuch et al. |
| 5,926,762 | A |  | 7/1999 | Arpee et al. |
| 5,946,612 | A |  | 8/1999 | Johannson |
| 5,987,306 | A |  | 11/1999 | Nilsen et al. |
| 5,991,622 | A |  | 11/1999 | Henry, Jr. |
| 6,031,455 | A | * | 2/2000 | Grube et al. ............ 340/539.26 |
| 6,157,838 | A |  | 12/2000 | Di Huo et al. |

(Continued)

FOREIGN PATENT DOCUMENTS

DE    102004061331    6/2006

(Continued)

OTHER PUBLICATIONS

"TEMS™ Automatic WCDMA: Take Control of Your Mobile Internet Quality of Service," www.ericsson.com; Publication AE/LZT 123 6694 R1; date of publication unknown (copyright 2001); two pages.
"TEMS™ Drive Tester CDMA: An Innovative Drive Test Solution," www.ericsson.com/tems; Publication AE/LZT 123 7307, R3; date of publication unknown (copyright 2003); four pages.

(Continued)

*Primary Examiner*—Brent Swarthout
(74) *Attorney, Agent, or Firm*—Alston & Bird, LLP

(57) ABSTRACT

Generally described, embodiments of the present invention provide systems and methods for gathering and disseminating travel conditions. These conditions may include traffic congestion and air quality data such as CO, $NO_x$, and Ozone ($O_3$) concentration levels, or meteorological conditions. In some embodiments, fleet vehicles already operating within a given area are equipped with monitoring devices to collect the desired data. The collected data may be transmitted to a central computer that associates the data with a road map and disseminates the data to the public. Dissemination may occur in a variety of ways including providing the data to radio stations for broadcast, posting the data on a website or pushing the data to navigation systems in vehicles or mobile communications devices such as cell phones and personal data assistants (PDAs).

27 Claims, 7 Drawing Sheets

U.S. PATENT DOCUMENTS

| | | | |
|---|---|---|---|
| 6,169,896 B1 | 1/2001 | Sant et al. | |
| 6,272,337 B1 | 8/2001 | Mount et al. | |
| 6,282,486 B1 | 8/2001 | Bates et al. | |
| 6,304,816 B1* | 10/2001 | Berstis | 701/117 |
| 6,315,255 B1 | 11/2001 | Chan et al. | |
| 6,336,035 B1 | 1/2002 | Somoza et al. | |
| 6,400,690 B1 | 6/2002 | Liu et al. | |
| 6,449,485 B1 | 9/2002 | Anzil | |
| 6,570,529 B2 | 5/2003 | Richton et al. | |
| 6,603,966 B1 | 8/2003 | Sheffield | |
| 6,711,404 B1 | 3/2004 | Arpee et al. | |
| 6,711,408 B1 | 3/2004 | Raith | |
| 6,853,842 B1 | 2/2005 | Wilson et al. | |
| 6,915,128 B1 | 7/2005 | Oh | |
| 6,919,821 B1 | 7/2005 | Smith | |
| 6,928,280 B1 | 8/2005 | Xanthos et al. | |
| 6,931,235 B2 | 8/2005 | Kline et al. | |
| 7,031,663 B2* | 4/2006 | Heinonen et al. | 455/67.11 |
| 7,062,264 B2 | 6/2006 | Ko et al. | |
| 7,099,669 B2 | 8/2006 | Sheffield | |
| 7,113,793 B2 | 9/2006 | Veerasamy et al. | |
| 7,236,779 B2 | 6/2007 | Lahav et al. | |
| 7,248,159 B2* | 7/2007 | Smith | 340/539.13 |
| 7,251,558 B1* | 7/2007 | McGrath | 701/117 |
| 2002/0029108 A1 | 3/2002 | Liu et al. | |
| 2003/0014286 A1 | 1/2003 | Cappellini | |
| 2003/0169812 A1 | 9/2003 | Wilhelm | |
| 2003/0224806 A1 | 12/2003 | Hebron | |
| 2004/0090628 A1* | 5/2004 | Ershov et al. | 356/438 |
| 2005/0131627 A1 | 6/2005 | Ignatin | |
| 2005/0140523 A1 | 6/2005 | Publicover | |
| 2006/0164232 A1 | 7/2006 | Waterhouse et al. | |

FOREIGN PATENT DOCUMENTS

| | | |
|---|---|---|
| EP | 0 977 450 A2 | 2/2000 |
| EP | 1113268 | 7/2001 |
| EP | 1 229 508 | 8/2002 |
| EP | 1566665 | 8/2005 |
| FR | 2710767 | 9/1993 |
| FR | 2831665 | 10/2001 |
| JP | 3251351 | 11/1991 |
| JP | 3062509 | 7/1999 |
| JP | 2000059292 | 2/2000 |
| JP | 2000295168 | 10/2000 |
| JP | 2001024577 | 1/2001 |
| JP | 2001218252 | 8/2001 |
| JP | 2002112302 | 4/2002 |
| JP | 2002335202 | 11/2002 |

OTHER PUBLICATIONS

Sigler, Lisa; "Assess speech quality with PESQ, now in TEMS™ Automatic;" date of publication unknown; one page.

"TEMS™ Automatic: Streamlined Operations and Improved QoS: GSM/GPRS, CDMA, and TDMA," www.ericsson.com/tems; Publication 287 01-FAP 901 0409 B; date of publication unknown (copyright 2004); four pages.

"TEMS™—Making Wireless Better," by Ericcson; APAC Workshop (Sep. 2004); seventeen pages.

"TechNotes: Tools for Precision: A Tool Kit to Optimize WCDMA Networks," www.ericsson.com/tems; date of publication unknown; one page, numbered p. 46.

Sigler, Lisa, Editor; "TEMS™ News," an Ericsson Newsletter (No. 2, Jun. 2003); eight pages.

Sigler, Lisa, Editor; "TEMS™ News," an Ericsson Newsletter (No. 2, Q2 2004); eight pages.

Sigler, Lisa, Editor; "TEMS™ News," an Ericsson Newsletter (No. 3, Q3 2004); eight pages.

Hedin, Lars-Göran, Editor; "On: The New World of Communication," an Ericsson global customer magazine (Mar. 2002); sixteen pages.

"TEMS™ Tech Support: TEMS Automatic GSM: Take Control of Your Mobile Internet Quality of Service," www.ericsson.com/services/tems/support/automatic/sup_automatic_gsm.shtml; date of publication unknown; three pages.

"TEMS™ Automatic: Making Wireless Better: Take Control of Your Mobile Internet Quality of Service," www.ericsson.com/services/tems/cdma/automatic-cdma.shtml; date of publication unknown; two pages.

"TEMS™ Tech Support: TEMS DriveTester CDMA: Making Wireless Better: Instantly Isolate Network Trouble Spots," www.ericsson.com/services/tems/support/drivetester/sup_drivetester_cdma.shtml; date of publication unknown; two pages.

"TEMS™ Tech Support: TEMS DriveTester GSM/TDMA: Making Wireless Better: Instantly Isolate Network Trouble Spots," www.ericsson.com/services/tems/support/drivetester/sup_drivetester_gsm_tdma.shtml; date of publication unknown; two pages.

"TEMS™ Tech Support: TEMS LinkPlanner: Making Wireless Better: FAQ's," www.ericsson.com/services/tems/support/linkplanner/sup_linkplanner_faq_import.shtml; date of publication unknown; two pages.

"TEMS™ Tech Support: TEMS LinkPlanner: Making Wireless Better: FAQ's Map Data," www.ericsson.com/services/tems/support/linkplanner/sup_linkplanner_faq_mapdata.shtml; date of publication unknown; one page.

"TEMS™ Tech Support: TEMS LinkPlanner: Making Wireless Better: FAQ's General," www.ericsson.com/services/tems/support/linkplanner/sup_linkplanner_faq_general.shtml; date of publication unknown; one page.

"TEMS™ DriveTester CDMA2000 2.0: An Innovative Drive Test solution for CDMA Networks," www.ericsson.com/products/TEMSdrivetesterCDMA200020pos.shtml; date of publication unknown; one page.

"TEMS™ Drive Tester CDMA: An Innovative Drive Test Solution," www.ericsson.com/tems; Publication 287 01-FAP 901 0539 Uen; date of publication unknown (copyright 2005); four pages.

Search Report dated Jun. 19, 2008, PCT/US06/27041, Filed Jul. 12, 2006.

Tai, "Urban Gas Monitoring System Using Optical Sensors," Proceedings of the SPIE, Jan. 1999, vol. 3746, pp. 332-336.

Wischoff, et al., "SOTIS- a Self-Organizing Traffic Information System," VTC 2003-Spring, the 57th IEEE Semiannual Vehicular Technology Conference, Jeju Korea Apr. 22-25, 2003, vol. 4, pp. 2442-2446.

International Search Report dated Oct. 10, 2008, PCT/US2007/011447, Filed Oct. 5, 2007.

International Searching Authority; International Search Report and Written Opinion, mailed Feb. 24, 2005; regarding International Application No. PCT/US2004/030934, "Symbiotic System for Testing Electromagnetic Signal Coverage in Areas Near Transport Routes" (European Patent Office).

International Searching Authority; International Search Report and Written Opinion, mailed Feb. 24, 2005; regarding International Application No. PCT/US2004/030930, "Network Testing Systems and Methods" (European Patent Office).

Office Communication from corresponding U.S. Appl. No. 10/947,548 Dated Jan. 24, 2008.

Office Communication from corresponding U.S. Appl. No. 10/947,548 Dated Jul. 9, 2008.

Office Communication from corresponding U.S. Appl. No. 10/947,548 Dated Nov. 25, 2008.

Office Communication from corresponding U.S. Appl. No. 10/763,875 Dated Mar. 10, 2006.

Office Communication from corresponding U.S. Appl. No. 10/763,875 Dated Jul. 18, 2007.

Office Communication from corresponding U.S. Appl. No. 10/763,875 Dated Feb. 25, 2008.

Office Communication from corresponding U.S. Appl. No. 10/763,875 Dated Nov. 5, 2008.

* cited by examiner

SYSTEMS AND METHODS FOR MONITORING TRAVEL CONDITIONS

BACKGROUND OF THE INVENTION

Prior to leaving home, commuters often seek information related to the conditions they will experience en route and areas in which they should avoid. This information may also be useful while en route so they can change their rout on the fly. Conditions important to most commuters include travel congestion and environmental conditions along their planned route. For the information to be useful, it must be timely provided such that an individual can alter their route in response to the information.

Regarding traffic congestion, there are many available systems that provide traffic conditions for particular roads, including expressway cameras and strips placed across the road to count the number of cars that pass. In some metropolitan areas, radio stations and television stations broadcast traffic conditions based on information received from expressway cameras, police reports and eyewitnesses accounts either from persons caught in traffic or helicopters overhead. In some cases, the speed of probe vehicles is monitored. This information is often focused on major expressways and does not provide a comprehensive picture of the overall traffic situation. Additional information would be helpful to commuters because they typically spend at least a portion of their commute on roads not monitored by these systems. Accordingly a need exists for systems that provide a more comprehensive traffic congestion picture to replace or supplement current systems.

In addition to avoiding traffic congestion, a commuter may also wish to avoid areas experiencing certain environmental conditions such as high air pollution concentrations. This would be especially true for individuals with asthma or other medical conditions that make them sensitive to air pollutants. Although traffic conditions are currently provided via radio or television broadcasts on a limited basis, other travel conditions such as air quality are not typically provided. Accordingly, a need exists for improved systems and methods to collect and disseminate air quality data.

Present air quality monitors collect useful data, however the systems are typically limited to a few collection sites. For effective analysis, data should be gathered over a large geographic area at approximately the same time so a comprehensive picture of the area can be obtained. A need exists for systems and methods of collecting and analyzing travel condition data to evaluate pollution patterns and factors affecting changes in air quality.

Data relating to travel conditions can also be important for long term planning and evaluating remedial measures. For example, traffic congestion and air quality data may be useful to city planners when evaluating where to build roads, land use issues and zoning requests. Traffic engineers may also use this data to identify traffic congestion issues and the factors affecting traffic congestion. Present systems, such as the traffic cameras and eyewitness accounts do not provide data useful in making these evaluations. Car counters and probe vehicles provide some useful information, but the breadth of information is limited. What is needed is a comprehensive system that collects high quality data over a large collection period such that factors effecting travel conditions may be evaluated.

BRIEF SUMMARY OF THE INVENTION

Generally described, embodiments of the present invention provide systems and methods for gathering and disseminating travel conditions that address some of the deficiencies in the state of the art, some of which are discussed above. These conditions may include traffic congestion and air quality data such as CO, NOx, and Ozone (O3) concentration levels, or meteorological conditions. In some embodiments, fleet vehicles already operating within a given area are equipped with monitoring devices to collect the desired data. The collected data may be transmitted to a central computer that associates the data with a road map and disseminates the data to the public. Dissemination may occur in a variety of ways including providing the data to radio stations for broadcast, posting the data on a website or pushing the data to navigation systems in vehicles or mobile communications devices such as cell phones and personal data assistants (PDAs).

In one embodiment, a system for collecting air quality data for a geographic area is provided. The system includes a vehicle equipped with an air quality monitoring device which is configured to collect air quality data including the concentration of at least one pollutant and the physical location of said vehicle; and a controller configured to receive said air quality data from said air quality monitoring device and further configured to transfer said air quality data to a central computer, wherein said central computer is configured to analyze said air quality data and to disseminate the results of said analysis in near real time such that recipients can alter their behavior based in part on said results.

In a further embodiment, a method for collecting and analyzing traffic congestion information is provided. The steps of this method include: collecting a plurality of data points for a plurality of vehicles operating in a geographic area according to a dispatch plan identifying a plurality of scheduled stops, wherein each of said data points includes both vehicle speed and vehicle location; transmitting said data to a central computer; segregating a subset of said plurality of data points by filtering out data points collected when said vehicle is within a predetermined distance from said scheduled stops; and associating said subset with a digital map of said geographic area.

In another embodiment, a method for collecting and analyzing ambient condition information is provided. The method includes the steps of: collecting a plurality of speed data points for a plurality of vehicles operating in a geographic area according to a plurality of dispatch plans identifying a plurality of scheduled stops wherein said speed data includes both vehicle speed and vehicle location; collecting a plurality of air quality data points for said plurality of vehicles wherein said air quality data points include the concentration of at least one pollutant and vehicle location; transmitting said speed data points and said air quality data points to a central computer; segregating a subset of said plurality of speed data points by filtering out speed data points collected when said vehicle is within a predetermined distance from said scheduled stops; associating said subset of speed data points and said air quality data points with a digital map of said geographic area; and disseminating results of said associating step.

In another embodiment, a system is provided for collecting ambient condition information for a geographic area. The system includes a plurality of vehicles dispatched to perform tasks other than data collection in a geographic area, a plurality air quality monitoring devices installed in said plurality of vehicles configured to collect air quality data including the concentration of at least one pollutant and the physical location of an associated vehicle, a plurality of speed monitoring devices installed in said plurality of vehicles configured to collect speed data related to the speed of their associated vehicle and the physical location of their associated vehicle where each of said vehicles including one or more data radios for communicating said air quality data and said speed data and a central computer configured to receive and analyze said air quality data and said speed data from said one or more data radios.

In a further embodiment, a system for collecting meteorological data for a geographic area is provided. This system includes a plurality of vehicles dispatched to perform tasks other than data collection in a geographic area, a plurality meteorological sensors installed in said plurality of vehicles configured to collect meteorological data including the physical location of an associated vehicle, each of said vehicles including one or more data radios for communicating said meteorological data and a central computer configured to receive and analyze said meteorological data from said one or more data radios.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention will now be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Moreover, many modifications and other embodiments of the inventions set forth herein will come to mind to one skilled in the art to which these inventions pertain having the benefit of the teachings presented in the foregoing descriptions and the associated drawings. Like numbers refer to like elements throughout.

General Description and Operation

Generally described, embodiments of the present invention provide systems and methods for gathering and disseminating travel conditions. These conditions may include, without limitation, traffic congestion and air quality data such as CO, $NO_x$, and Ozone ($O_3$) concentration levels. In some embodiments, fleet vehicles already operating within a given area are equipped with monitoring devices to collect the desired data. Examples of suitable vehicles for this type of data gathering include, without limitation, those operated by courier services, public transportation, taxis, utility meter readers, refuse collection vehicles or private home service companies. The symbiotic relationship created by vehicles performing their primary tasks and simultaneously gathering data allows the collection of data over a large geographic area at a reduced cost.

In further embodiments of the present invention, the collected data is transmitted to a central computer that associates the data with a road map and disseminates the data to the public. Dissemination may occur in a variety of ways including providing the data to radio stations for broadcast, posting the data on a website or pushing the data to navigation systems in vehicles or mobile communications devices such as cell phones and personal data assistants (PDAs). Additionally, the central computer may also analyze data collected over time to measure average conditions or to identify trends and correlations between times, events or other parameters and traffic congestion or air quality or other conditions along the route. The data may also be used by government agencies or other interested groups to develop strategies for combating pollution and setting public policy.

Data Collection System

Figure 1:
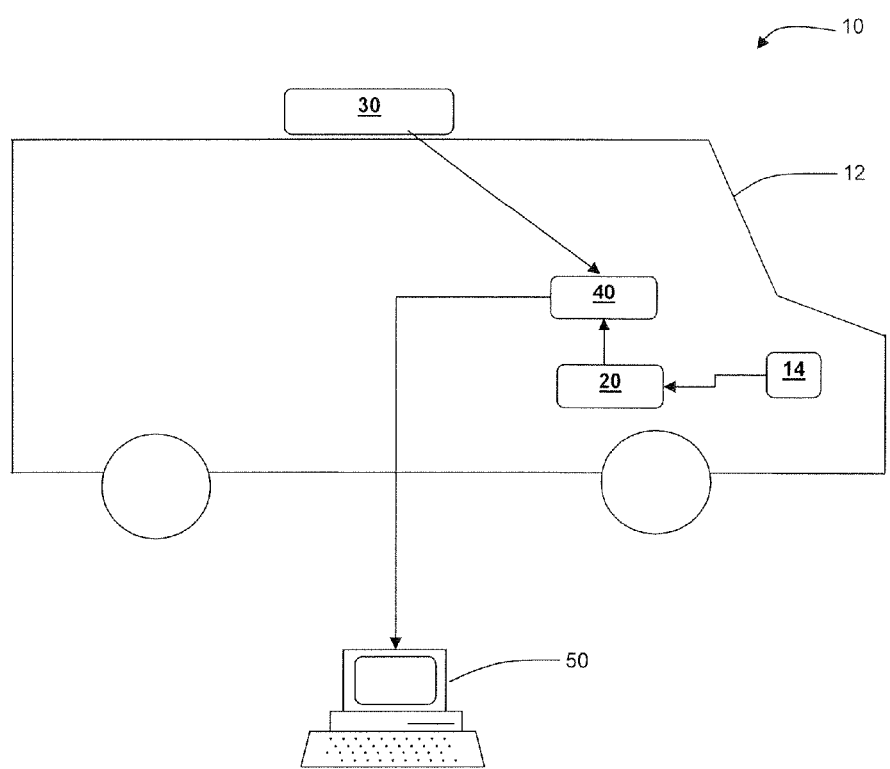
FIG. 1 is a schematic drawing providing a high level view of a data collection system in accordance with an embodiment of the present invention.

In FIG. 1, an embodiment of the present invention is illustrated where a vehicle 12 is equipped with a data collection system 10. The data collection system 10 includes a speed monitoring device 20, an air quality monitoring device 30, and a controller 40. In the illustrated embodiment, the speed monitoring device 20 and the air quality monitoring device 30 are distinct telematics type devices that collect and communicate travel condition data to the controller 40. However, as one of ordinary skill in the art will appreciate, the functions performed by these three separate devices may be consolidated into one or more devices as desired.

Speed Monitoring Device

Figure 2:
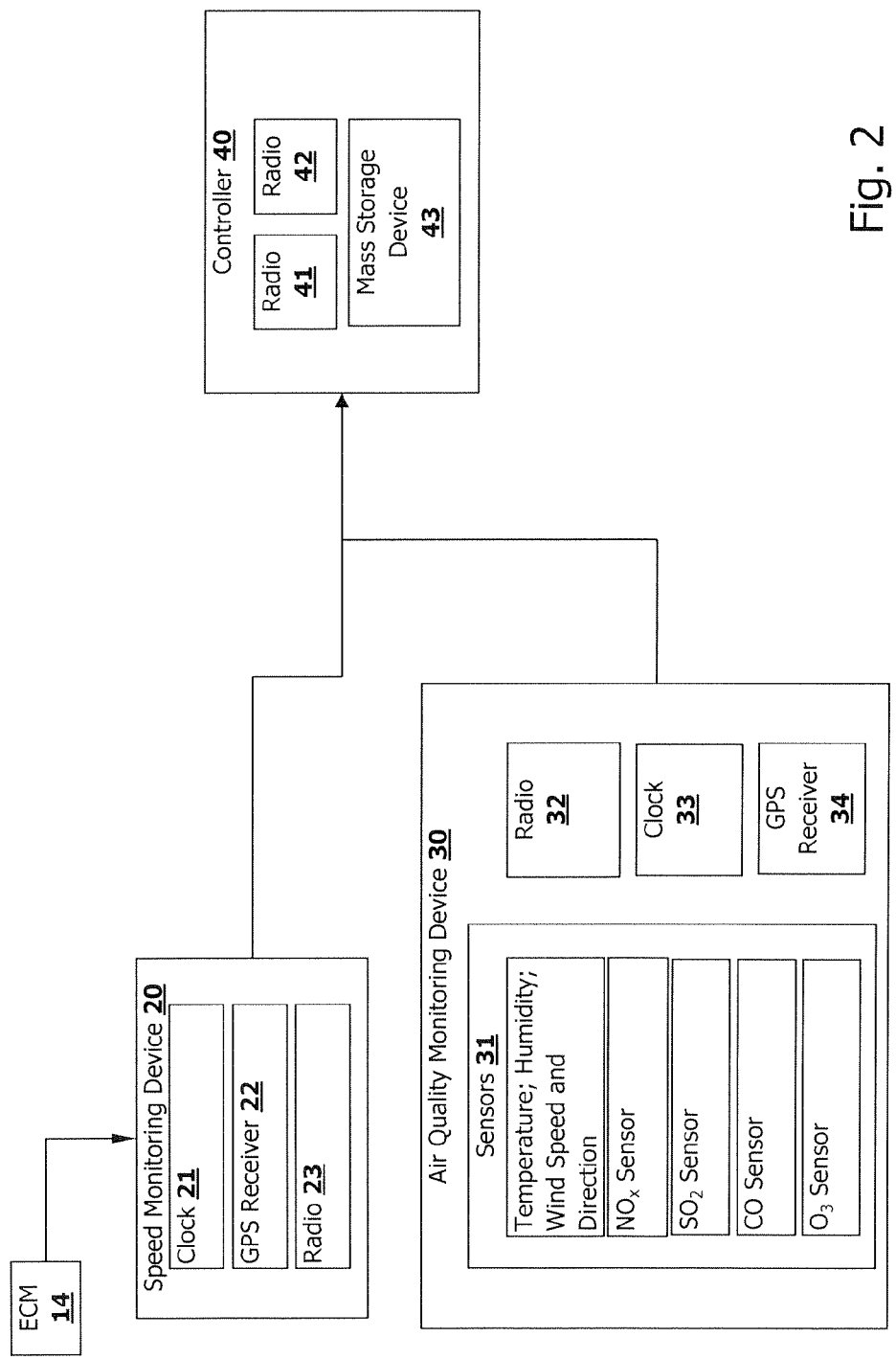
FIG. 2 is a schematic drawing illustrating the components of a data collection system 10 in accordance with an embodiment of the present invention.

Referring to FIG. 2, an embodiment of the speed monitoring device 20 includes a J-Bus protocol interface that provides access to the vehicle's engine control module 14 ("ECM"). As one of ordinary skill in the art will appreciate, most modern vehicles are equipped with an ECM that receives data from various sensors, including vehicle speed, for the purpose of controlling both emissions and engine operation. The speed monitoring device 20 is configured to receive a vehicle speed signal from the ECM 14 and to communicate the monitored speed to the controller 40. The speed monitoring device may also include an internal clock 21 that time stamps the data and a global positioning satellite (GPS) receiver 22 for determining the global location of the vehicle 12 during a data collection event. Accordingly the speed data communicated to the controller 40 may include the vehicle speed, the vehicle location and a time stamp for each data collection event.

In an alternative embodiment, the speed monitoring device is configured with its own speed sensor and therefore would not utilize the vehicle's ECM. In a further embodiment, the controller 40 may receive the speed data directly from the ECM.

The illustrated speed monitoring device 20 also includes a data radio 23 to facilitate communication between the speed monitoring device 20 and the controller 40. In one embodiment, a wireless personal area network (WPAN) data radio 23 provides the communication link. In this embodiment, any wireless communication standard may be used such as Bluetooth™ (IEEE 802.15.1 standard compatible) or any other standard in the IEEE 802 family of standards. The IEEE 802 family of standards are hereby incorporated by reference in their entirety and made a part hereof. One of ordinary skill in the art will readily recognize that other wireless protocols exist or may be developed that can be used with the present invention. In an alternative embodiment, the speed monitoring device 20 utilizes a wired connection to communicate to the controller 40 in place of the data radio 23.

Air Quality Monitoring Device

The air quality monitoring device 30 in accordance with an embodiment of the present invention includes a series of environmental sensors 31 for detecting ambient air quality. In one embodiment, the air quality monitor 30 includes one or more gas sensors that detect the concentration of common pollutants such as carbon monoxide (CO), nitrogen oxides (NOx), sulfur oxides (SOx) and ozone ($O_3$). The devices may also include sensors that have the capability to sample for hydrogen sulfide ($H_2S$) and ammonium ($NH_4$) or other airborne substances including particulates.

In addition to gas concentration monitoring, the air quality monitoring device may also include meteorological sensors to monitor ambient conditions such as temperature, barometric pressure, relative humidity, precipitation and wind speed. Telematics type devices may also be utilized to monitor meteorological conditions. For example, precipitation may be indicated if the vehicle's windshield wipers are activated. This data may be used to provide more granular picture of current weather conditions than can be provided by a few stationary weather collection sites scatter throughout a geographic area. In some embodiments, the air quality monitoring device may only employ meteorological sensors.

As with the speed monitoring device 20, the air quality monitoring device 30 may include a data radio 32 to facilitate communication of collected data to the controller 40. Alternatively, the communication link between the air quality monitoring device 30 and the controller 40 is a wired connection.

It should be understood that any type of gas sensor may be used in connection with the present invention such as electrochemical, electro-mechanical (MEMS), solid state or infrared. Typically, the sensors will detect the concentration of a particular gas in parts per million (ppm) or parts per billion (ppb).

Similar to the speed monitoring device, the air quality monitoring device 30 may also include an internal clock 33 for time stamping the data and a GPS receiver to determine the global location of the vehicle when data is collected. The air quality monitoring device 30 communicates air quality data including pollutant concentrations, a time stamp and a global location with each air quality data collection event.

Controller

Generally described, the controller 40 communicates data received from the speed monitoring device 20 and the air quality monitoring device 30 to the central computer 50. In one embodiment, the controller 40 includes a WPAN data radio 41 configured to provide a communication link with the monitoring devices to facilitate receipt of collected data. The data radio 41 may utilize any wireless communication standard such as for example, Bluetooth™ (IEEE 802.15.1 standard compatible) or any other IEEE 802 family of standards. Alternatively, the controller may receive data from the monitoring devices via a wired connection using standard interfaces, such as RS-232, RS422, DIN, USB or other known or developed interface.

In addition to the communication link with the monitoring devices, the controller 40 also provides a communication link with the central computer 50. In one embodiment, the communication link is provided by a data radio 42, which utilizes standard 3G wireless telecommunications protocols, such as CDMA2000 1× EV-DO, GPRS, W-CDMA, or other protocol. In an alternative embodiment, the data radio 42 may utilize wireless IEEE 802.11 or 802.15.4 protocols.

In a further embodiment, the controller 40 includes a mass storage device 43, which writes the received data to a storage media (not shown) such as floppy disks, hard disks, compact disks, DVDs, memory cards or any other type of mass storage media type known or developed. This storage media could be used when wireless connections are unavailable or when dissemination of the data is not time sensitive. In this embodiment, the data on the storage media could be transferred to the central computer 50 at the end of a shift by transferring the storage media itself to the central computer or to a local computer having a communication link with the central computer via a network such as the Internet, an intranet or a LAN.

In an alternative embodiment, the functions of the controller are incorporated into the speed monitoring device 20 and the air quality monitoring device 30. For example, data radios in the two monitoring devices may be configured to communicate directly with the central computer.

Central Computer

Figure 3:
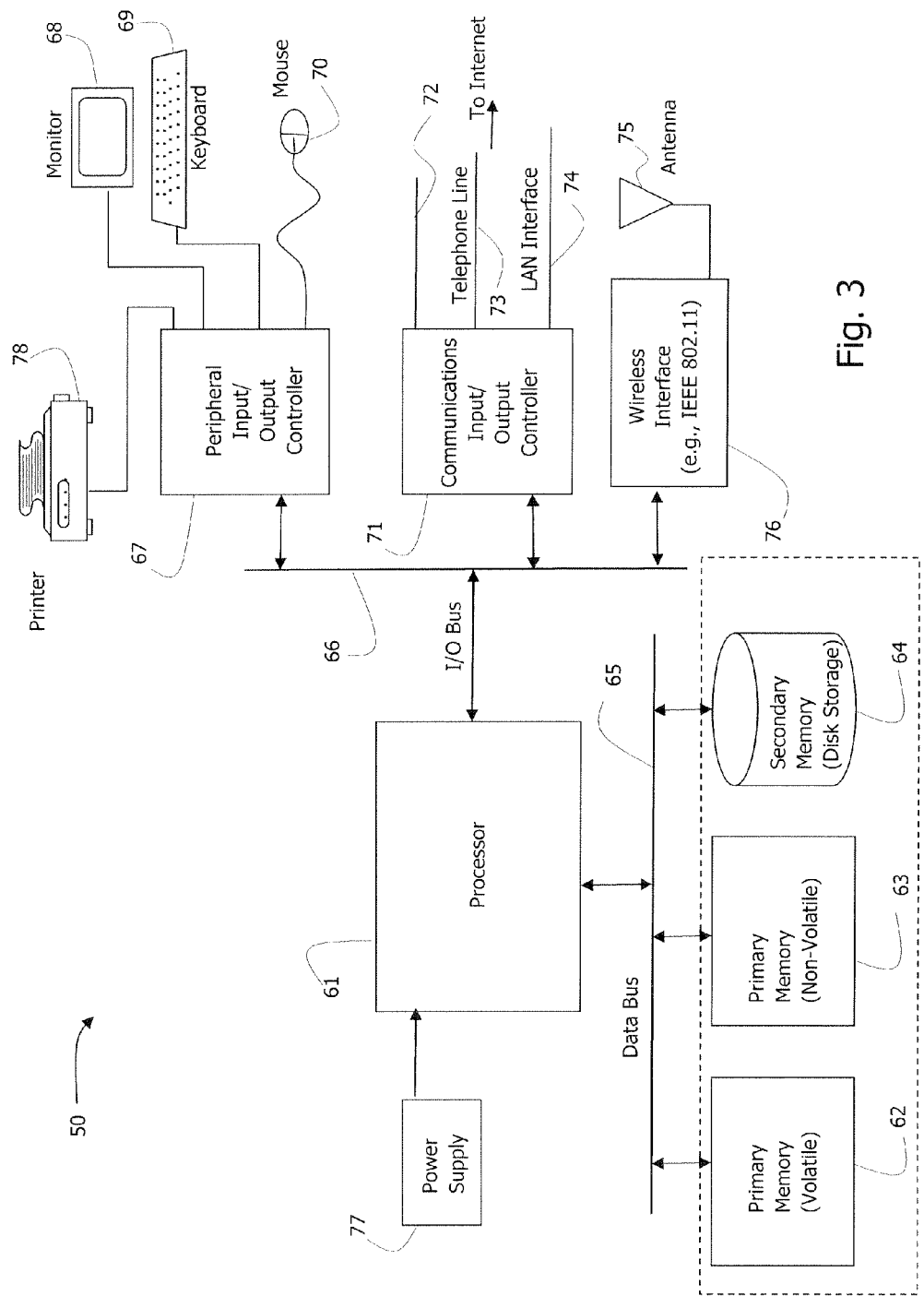
FIG. 3 is a schematic drawing illustrating an exemplary architecture of a central computer in accordance with an embodiment of the present invention.

The central computer 50 analyzes and stores the data collected by the monitoring devices. The general architecture and capabilities of the central computer 50 will now be described with reference to FIG. 3. A processor 61, such as a microprocessor, is used to execute software instructions for carrying out defined steps such as analyzing data received from the monitoring devices. The processor receives power from a power supply 77 that also provides power to the other components as necessary. The processor 61 communicates using a data bus 65 that is typically 16 or 32 bits wide (e.g., in parallel). The data bus 65 is used to convey data and program instructions, typically, between the processor and memory. In the present embodiment, memory can be considered primary memory 62 that is RAM or other forms which retain the contents only during operation, or it may be non-volatile 63, such as ROM, EPROM, EEPROM, FLASH, or other types of memory that retain the memory contents at all times. The memory could also be secondary memory 64, such as disk storage, that stores large amount of data. In some embodiments, the disk storage may communicate with the processor using an I/O bus 66 instead or a dedicated bus (not shown). The secondary memory may be a floppy disk, hard disk, compact disk, DVD, or any other type of mass storage device known to those skilled in the arts. As discussed above, data may be transferred to the central computer from the controller using a mass storage device.

The processor 61 also communicates with various peripherals or external devices using an I/O bus 66. In the present embodiment, a peripheral I/O controller 67 is used to provide standard interfaces, such as RS-232, RS422, DIN, USB, or other interfaces as appropriate to interface various input/output devices. Typical input/output devices include local printers 78, a monitor 68, a keyboard 69, and a mouse 70 or other typical pointing devices (e.g., rollerball, trackpad, joystick, etc.).

The processor 61 may also communicate using a communications I/O controller 71 with external communication networks, and may use a variety of interfaces such as data communication oriented protocols 72 such as X.25, ISDN, DSL, cable modems, etc. The communications controller 71 may incorporate a modem (not shown) for interfacing and communicating with a standard telephone line 73. Finally, the communications I/O controller may incorporate an Ethernet interface 74 for communicating over a LAN. Any of these interfaces may be used to access the Internet, intranets, LANs, or other data communication facilities.

Finally, the processor 61 may communicate with a wireless interface 76 that is operatively connected to an antenna 75 for communicating wirelessly with another devices, using for example, one of the IEEE 802.11 protocols, 802.15.4 protocol, or a standard 3G wireless telecommunications protocols, such as CDMA2000 1× EV-DO, GPRS, W-CDMA, or other protocol. As discussed above, the controller may transmit collected data to the central computer using one of the wireless protocols.

Figure 4:
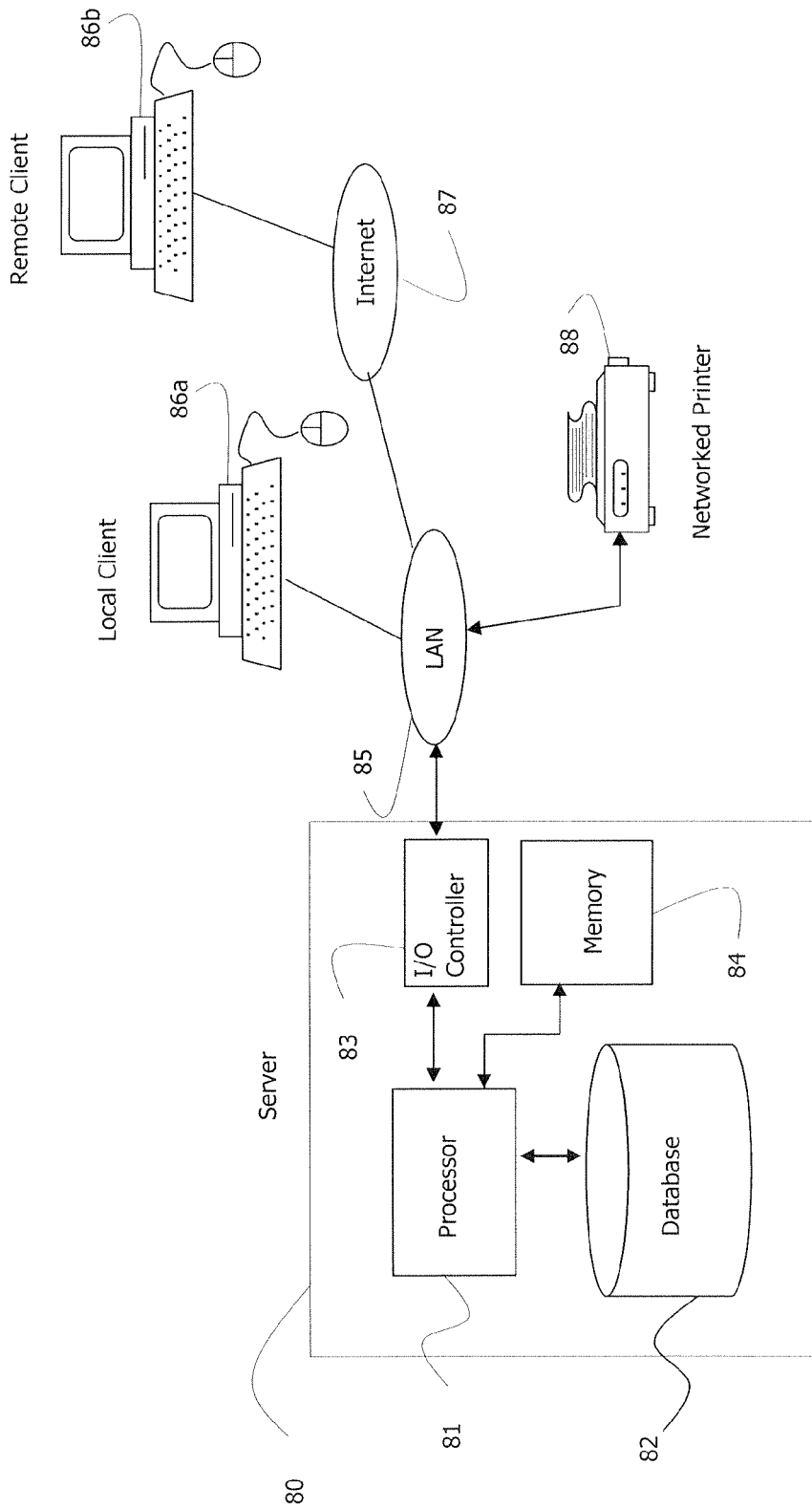
FIG. 4 is a schematic drawing illustrating an exemplary distributed processing architecture of a central computer in accordance with an embodiment of the present invention.

An alternative embodiment of the central computer 50 is the processing system shown in FIG. 4. In this embodiment, a distributed communication and processing architecture is shown involving a server 80 communicating with either a local client computer 86a or a remote client computer 86b. The server 80 typically comprises a processor 81 that communicates with a database 82, which can be viewed as a form of secondary memory, as well as primary memory 84. The processor also communicates with external devices using an I/O controller 83 that typically interfaces with a LAN 85. The LAN may provide local connectivity to a networked printer 88 and the local client computer 86a. These may be located in the same facility as the server, though not necessarily in the same room. Communication with remote devices typically is accomplished by routing data from the LAN 85 over a communications facility to the Internet 87. A remote client computer 86b may execute a web browser, so that the remote client 86b may interact with the server as required by transmitted data through the Internet 87, over the LAN 85, and to the server 80.

Those skilled in the art of data networking will realize that many other alternatives and architectures are possible and can be used to practice the principles of the present invention. The embodiments illustrated in FIGS. 3 and 4 can be modified in different ways and be within the scope of the present invention as claimed.

Methods of Use

Figure 5:
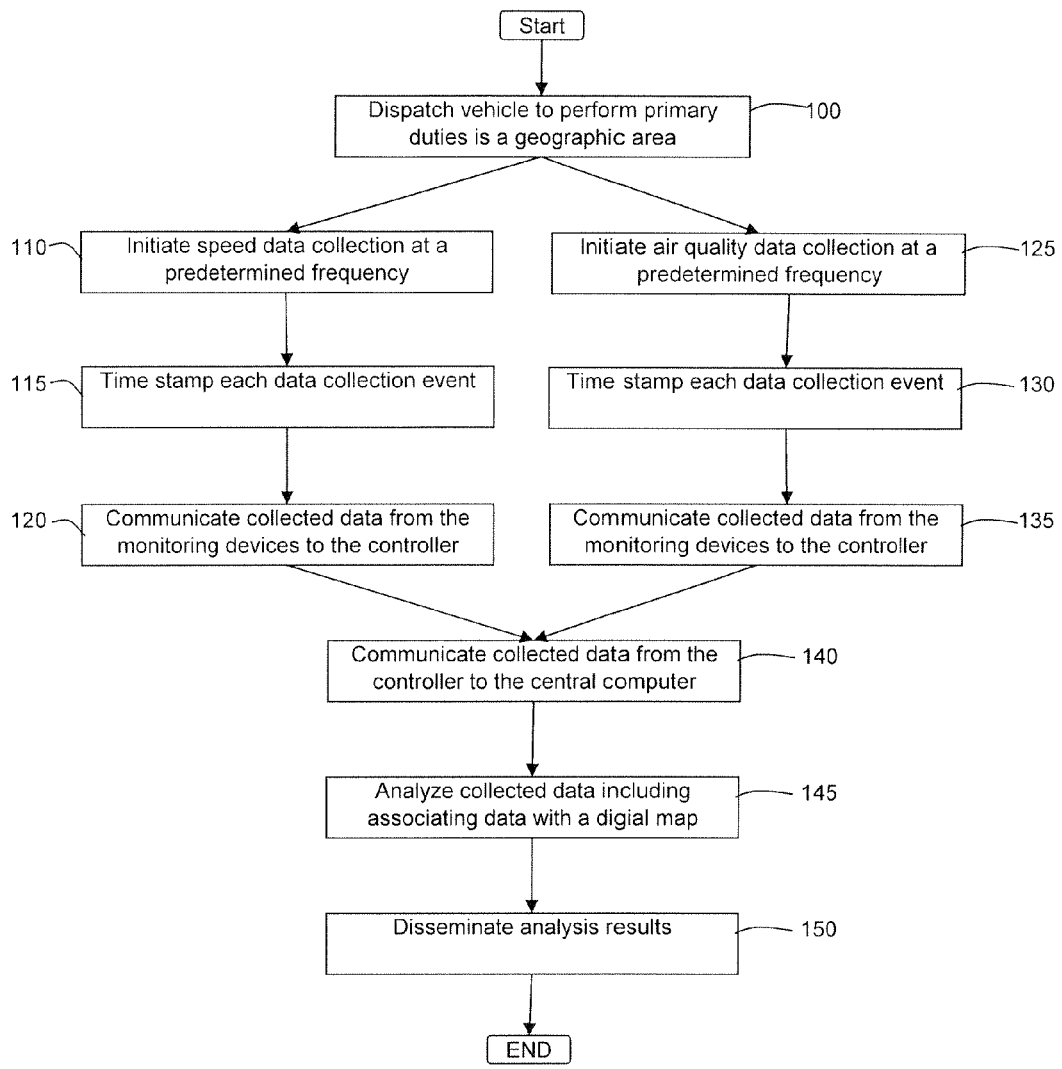
FIG. 5 is a flow diagram illustrating steps of an exemplary data collection method in accordance with an embodiment of the present invention.

FIG. 5 provides a flow chart illustrating an exemplary method of use for the data collection system 10 in accordance with an embodiment of the present invention. In this exemplary method, a data collection system 10 is installed into a fleet vehicle such as a parcel delivery vehicle and data is collected while the driver delivers packages. It should be understood that methods in accordance with embodiments of the present invention may utilize probe vehicles dispatched with the primary purpose of gathering data or vehicles dispatched for other purposes such as, without limitation, those operated by courier services, public transportation, taxis, utility meter readers, refuse collection vehicles or private home service companies.

In an exemplary parcel delivery context, the process begins at Step 100 where a parcel delivery vehicle is dispatched from a base of operations to pickup and deliver packages in a particular geographic area. The parcel delivery vehicle is equipped with a data collection system 10.

At Step 110, the speed monitoring device 20 of the data collection system 10 initiates data collection. Data collection means collecting data points which include the vehicle speed and the vehicle location. In one embodiment, the data collection is initiated as or after the delivery vehicle leaves the service center. This may be triggered by the driver or by predetermined vehicle conditions such as the vehicle's physical location, initial movement of the vehicle at the beginning of a shift or may be tied to the engine's ignition. The physical location may be determined by the GPS receiver in the speed monitoring device 20 and the trigger may be when the delivery vehicle enters or exits a particular geographic boundary.

Data collection by the speed monitoring device 20 occurs at a predetermined frequency such as performing a data collection event every eight seconds. At Step 115, the data collection for a particular event is time stamped. Then, at Step 120 the speed monitoring device 20 communicates the collected data to the controller 40.

Similarly, the air quality monitoring device 30 initiates data collection at Step 125. Data collection for this device means collecting air quality data points that include the concentration of at least one air pollutant and the location of the vehicle. As with the speed monitoring device, the air quality monitoring device 30 may be triggered by the driver or by predetermined vehicle conditions such as the vehicle's physical location, initial movement of the vehicle at the beginning of a shift or the start of the engine. It should be understood that the speed and air quality monitoring devices may or may not be triggered at the same time or by the same triggering mechanism. For example, the speed monitoring device 20 may be triggered by the start of the vehicle's engine while the air quality monitoring device 30 is triggered when the vehicle enters a predetermined geographic area as determined by its GPS receiver.

Data collection by the air quality monitoring device 30 occurs at a predetermined frequency. This frequency may or may not be the same as the frequency for the speed monitoring device 20. For example, the speed monitoring device may be configured to perform a data collection event every eight seconds while the air quality monitoring device may be configured to data collection event every three minutes.

At Step 130, data collected by the air quality monitoring device 30 for a given data collection event is time stamped, and the collected data communicated to the controller 40 at Step 135. In some embodiments, a vehicle identifier is also provided. This identifier would be useful where multiple vehicles are employed to gather data.

At Step 140, the controller 40 communicates the received data from the monitoring devices to the central computer 50. In one embodiment, the received data is transmitted shortly after receiving the data from one or both of the monitoring devices. Alternatively, the data received may be temporarily stored by the controller 40 and sent periodically to the central computer either based on a particular time schedule or based on a threshold volume of data temporarily stored.

At Step 145, the central computer analyzes and then disseminates the data received. The type of analysis performed depends, at least in part, on the audience that receives the data. For example, when disseminating to the public at large, the data may need to be analyzed quickly and presented in near real time (e.g. within minutes) and in a readily understandable form such that the receiving individuals can make decisions based on the data. On the other hand, if the data is being disseminated to an entity such as a government agency or other interested group, data collected over a certain period of time may be more valuable.

Figure 6:
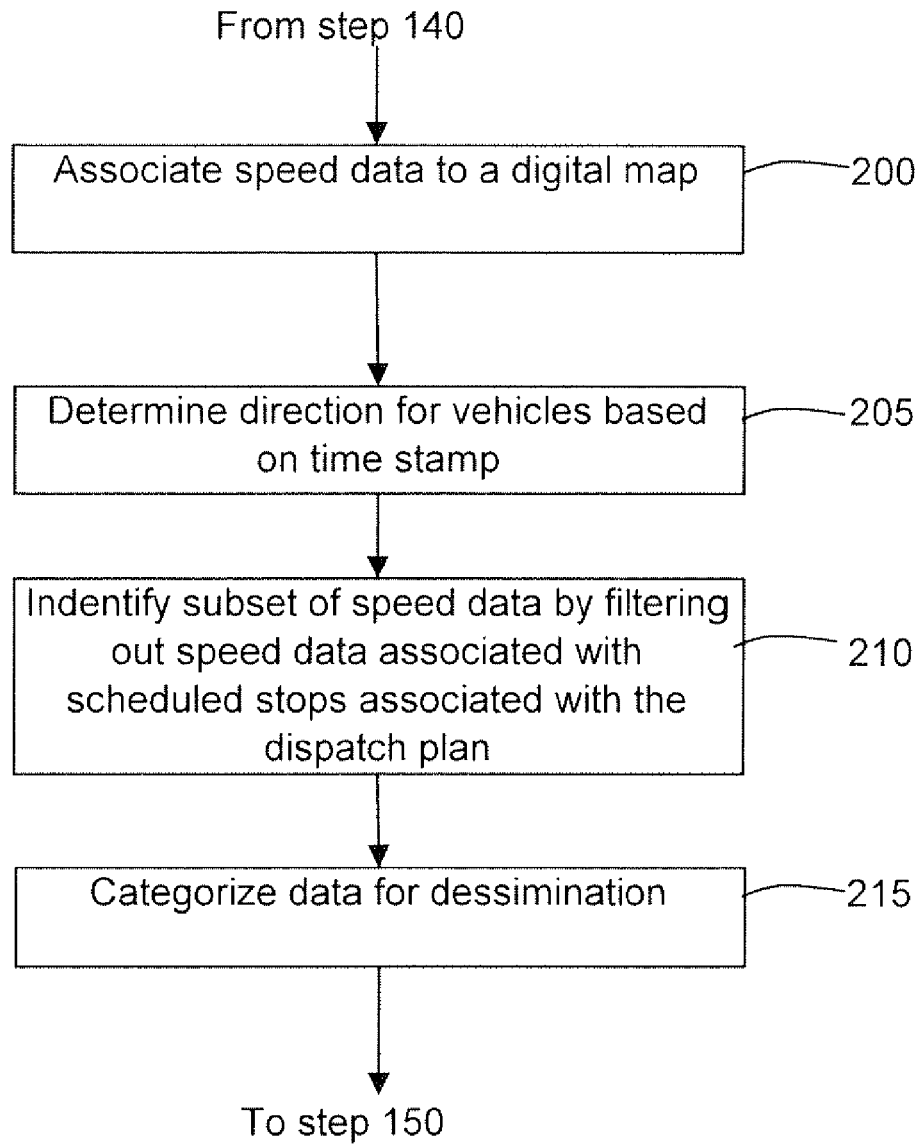
FIG. 6 is a flow diagram illustrating steps for analyzing speed and air quality data in preparation for dissemination.

Turning to FIG. 6, the steps for analyzing data in preparation for disseminating to the public at large is provided. At step 200, the central computer associates the speed or air quality data or both with a road map of the associated geographic area. This may be accomplished by associating the GPS physical location information provided by the speed and air quality monitoring devices with a digital road map such as those provided by Navteq™ or Tele Atlas™.

At Step 205, the location data for sequential speed data events is used to determine the direction of travel of the vehicle. With this information, the central computer can distinguish traffic congestion experienced in either direction on a particular road.

A consequence of using fleet vehicles already operating in a given geographic area to collect data is that the data may be skewed due to stops made in connection with the primary purpose of the fleet vehicles being in the geographic area. For example, if parcel delivery vehicles are used to collect data, stops made to deliver packages may skew the vehicle speed data. In one embodiment, the central computer filters out speed data for stops made by the vehicle that are associated with the dispatch purpose of the vehicle. This is performed by comparing the location information associated with each speed data collection event and the vehicle's dispatch plan which would identify the address of schedule stops.

Thus, at Step 210 speed data points having a geographic location within a predetermined distance threshold of the geographic location of a scheduled stop are filtered out. The remaining subset of data points are then analyzed and disseminated. In a parcel delivery context, a dispatch plan includes a sequence of street addresses associated with parcel deliveries and pickups for a given vehicle. The central computer may retrieve the dispatch plan for a delivery vehicle from the parcel delivery organization's legacy system. The street address is converted into a latitude/longitude coordinates for comparison with the location data associated with the vehicle speed. Speed data points having a location within a predetermined threshold distance (e.g., 100 feet) of the scheduled stop location would be filtered out leaving a subset of speed data points for analysis.

Dissemination to the public may take a number of different forms such as posting to an Internet website, a television broadcast or a radio broadcast. In a further embodiment, the information is pushed to navigation systems, cellular telephones, personal data assistants ("PDA") or other mobile communication devices.

To facilitate understanding by the public, the data may be categorized, color-coded and associated with a digital street map for display on a website, television broadcast, navigation system, PDA, cellular telephone or other mobile communication device at Step 215. Of course, the visual display may be described by an individual for a radio broadcast.

For air quality, the data may be categorized based on the overall concentration of pollutants such as parts per million or parts per billion. Alternatively, the categories may be based on an average person's sensitivity (e.g., clear, minor irritation, major irritation, hazardous). Each range may be associated with a color for presentation on the map thereby indicating which areas have elevated pollution levels. Furthermore, specific pollutants may be identified on the map if they exceed a predetermined threshold.

Similarly, the speed data may be categorized and color-coded based on particular speed ranges. In one embodiment, individual speed data points are categorized and color-coded. For example, different colors may be associated with speeds of 0-20 mph, 20-45 mph, 45-55 mph and over 55 mph. In an alternative embodiment, multiple speed data points are averaged for a given distance traveled on a particular road to determine the average speed. The average speed would then be categorized and color-coded as described above.

Alternatively, the time required to travel between particular landmarks may be calculated using the time stamp data for data points proximate the desired landmarks such as buildings, intersections or ramps. These times could also be categorized and color-coded. In a further embodiment, the speed data may be displayed on the map as travel times between specific intersections or landmarks. The direction of travel is preferably indicated for the speed data. Of course, any types of ranges or displays may be used in connection with embodiments of the present invention.

By providing the data directly to the public in near real time (e.g., within minutes), behavior patterns can be altered in response to the data. For example, individuals can determine an optimum route based on traffic congestion and pollution data.

In addition to providing data directly to the public, data may be provided to government agencies or other interested parties based upon a request. The request will typically include a time period and either a geographic area of interest or a landmark of interest. For this type of request, immediate reporting of individual data points is typically not needed. Rather, multiple data points are analyzed to determine trends and identify factors impacting travel conditions. To provide data for a given area of interest, the data for multiple vehicles may be aggregated and analyzed. When multiple vehicles are used to collect data, data points will typically include a vehicle identifier so the data points can be associated with the route taken by a specific vehicle.

When evaluating traffic congestion over time, it may useful to know the traffic congestion in the proximity of known landmarks such as expressway on-ramps, off-ramps, traffic signals and intersections. Traffic engineers may use this information for identifying traffic problems, and evaluating the impact of remedial measures. Embodiments of the present invention can analyze the data collected to provide this type of information.

Figure 7A:
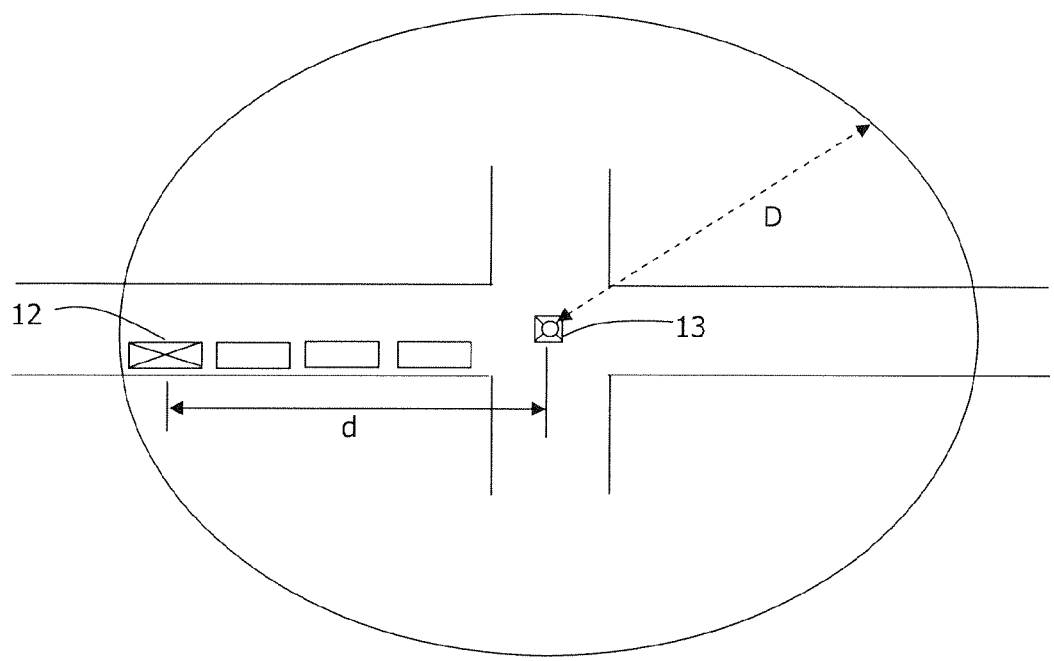
FIGS. 7A & 7B are schematic diagrams illustrating traffic congestion at an intersection and distances used in connection with embodiments of the present invention.
Figure 7B:
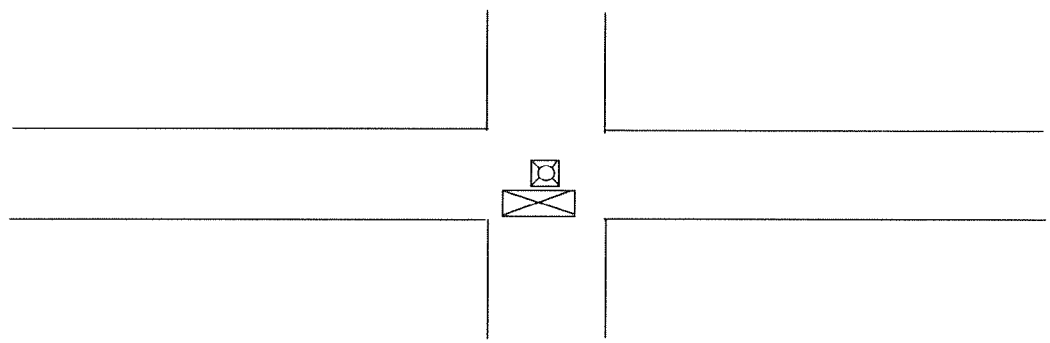

With reference to FIGS. 7A and 7B, the congestion entering an intersection may be evaluated using embodiments of the present invention. In one embodiment, the location and speed of a vehicle 12 equipped with a data collection system 10 (not shown) is analyzed in reference to a landmark, which in the illustrated example is an intersection having a traffic light 13.

After an intersection has been identified for evaluation, the central computer locates data points that have vehicle locations within a threshold distance "D" of the intersection. Using the time stamp and vehicle identifier data, the central computer can determine the movement of a particular vehicle as it approaches and exits the intersection. One measure of congestion is the distance "d" from an intersection in which the vehicle is forced to slow below a threshold speed or stop due primarily to the number of vehicles between it and the intersection as illustrated in FIG. 7A. In one embodiment, the distance "d" is calculated by comparing the geographic location associated with the zero vehicle speed data point and the geographic location of the intersection as provided by a digital map. Traffic engineers may use this data to evaluate the congestion relative to the traffic signal and the signal's effects on congestion.

In addition, embodiments of the present invention may determine the number of traffic light cycles necessary for the vehicle to enter the intersection from a stopped condition. In one embodiment, after determining the zero speed data points for a particular vehicle approaching the intersection, the central computer evaluates the time necessary to enter the intersection. This may be determined by comparing the time stamp for a zero speed data point (as shown in FIG. 7A) with the time stamp associated with a location proximate the center of the intersection for the same vehicle (as shown in FIG. 7B). The number of cycles could be calculated by the difference between the two time stamps divided by the cycle time of the traffic signal. Of course, the vehicle may stop several times before entering the intersection. In this case, the first occurrence of zero speed data within a predetermined threshold distance "D" would be used for this calculation.

In addition to using time to evaluate congestion related to traffic light cycles, an embodiment of the present invention may also count the number of zero speed data points for a particular vehicle approaching the intersection. The counting would occur after the vehicle is within a given threshold distance "D" from the intersection.

In further embodiments, data points may be identified where the vehicle speed is less than a threshold value as opposed to a zero vehicle speed condition. The same general types of calculations described above with regard to a zero speed condition may also be performed using data points having a vehicle speed value less than a threshold speed.

It should be understood that embodiments of the present invention may perform the above calculations for multiple vehicles within a give time period and provide statistical data as desired such as mean and standard distribution for a given landmark of interest.

There are numerous other factors that embodiments of the present invention may correlate with the traffic congestion data collected. For example, traffic congestion data may be correlated with the dates for events that draw large numbers of people, such as concerts, plays and sporting events. In this case, an embodiment may provide traffic congestion data for a given geographic area for a given time period such as an hour before the start of the event extending until an hour after the event. This data may be valuable to identify bottlenecks that may be alleviated for future events. Using this same technique, traffic congestion data may also be correlated with holidays.

An additional factor that may impact traffic congestion is the time of day. This data may be used to identify the start and end of the morning and afternoon "rush hours." In response to this data, the traffic signal cycles may be adjusted during rush hours to reduce the congestion.

Furthermore, weather conditions may also impact traffic congestion. The data collected by an embodiment of the present invention may be correlated with weather conditions such as the occurrence of rain, snow or fog that may be provided by an external source or onboard systems. Alternatively, the air quality monitoring device may include meteorological sensors capable of detecting the occurrence of rain, snow, temperature and fog.

The central computer 50 may also filter the air quality data collected. Under some circumstances, it may be desired to monitor the air quality in a specific geographic area such as near a suspected pollution source. The desired area may be a subset of data collected by one or more vehicles. The data collected using embodiments of the present invention may be filtered by the central computer to identify data points for a given geographic area. As will be understood by those skilled in the art, this filtering may be performed using the physical location information provided with each data collection event provided by monitoring devices in one or more vehicles. This data may be used to evaluate overall pollution in a given geographic area, to monitor a specific pollution source or to evaluate compliance with various regulations.

As with the speed data, the air quality data may be correlated with various parameters such as time of day, holidays, sporting events and weather conditions. Additionally the data may be correlated with the speed data.

CONCLUSION

In concluding the detailed description, those skilled in the art will understand that many variations and modifications can be made to the disclosed embodiments without substantially departing from the principles of the present invention. Also, such variations and modifications are intended to be included herein within the scope of the present invention as set forth in the appended claims.

It should be emphasized that the above-described embodiments of the present invention, particularly any "preferred embodiments" are merely possible examples of the implementations, merely set forth for a clear understanding of the principles of the invention. Variations and modifications may be made to the above-described embodiments of the invention without departing substantially from the spirit of the principles of the invention. All such modifications and variations are intended to be included herein within the scope of the disclosure and present invention and protected by the following claims.

That which is claimed:

1. A system for collecting air quality data for a geographic area comprising:
    a vehicle equipped with an air quality monitoring device which is configured to collect air quality data including the concentration of at least one pollutant and the physical location of said vehicle wherein data collection is triggered by the physical location of said vehicle; and
    a controller configured to receive said air quality data from said air quality monitoring device and further configured to transfer said air quality data to a central computer;
    wherein said central computer is configured to analyze said air quality data and to disseminate the results of said analysis in near real time such that recipients can alter their behavior based in part on said results.

2. The system of claim 1, wherein said vehicle is further equipped with a speed monitoring device for collecting data related to the speed of said vehicle and the physical location of said vehicle and wherein said speed data is transferred to said central computer via said controller and wherein further said central computer is configured to analyze and disseminate said speed data.

3. The system of claim 1, wherein said air quality data further comprise a time stamp.

4. The system of claim 1, wherein said central computer is configured to associate said air quality data with a digital map of said geographic area.

5. The system of claim 2, wherein said controller transfers said air quality data and said speed data to said central computer wirelessly.

6. The system of claim 1, wherein said dissemination comprises transmitting to a plurality of mobile communication devices.

7. The system of claim 1, wherein said air quality monitor is further configured to collect meteorological data.

8. The system of claim 1, wherein said central computer is further configured to correlated said air quality data with said speed data.

9. A method for collecting and analyzing traffic congestion information comprising the steps of:
    collecting a plurality of data points for a plurality of vehicles operating in a geographic area according to a dispatch plan identifying a plurality of scheduled stops, wherein each of said data points includes both vehicle speed and vehicle location;
    transmitting said data to a central computer;

segregating a subset of said plurality of data points by filtering out data points collected when said vehicle is within a predetermined distance from said scheduled stops; and associating said subset with a digital map of said geographic area.

10. The method of claim 9, further comprising the steps of:

identifying data points within said subset wherein both said vehicle speed is less than or equal to a threshold speed and said vehicle location is within a threshold distance from a landmark; and calculating the distance between said identified data points and said landmark.

11. The method of claim 9, wherein said data points include a time stamp and wherein said method further comprises the steps of:

identifying a first data point for one of said plurality of vehicles wherein both said vehicle speed is less than or equal to a threshold speed and said vehicle location is within a threshold distance from a landmark as identified by said digital map; and identifying a second data point for said one of said plurality of vehicles wherein said vehicle location is at a location proximate said landmark; and calculating the time difference between said first data point and said second data point.

12. The method of claim 9, wherein said landmark is an intersection.

13. The method of claim 9, wherein said landmark is an off ramp from an expressway.

14. The method of claim 9, wherein said landmark is a speed bump.

15. The method of claim 9, further comprising the steps of:

receiving event data relating to an event drawing a plurality of individuals;

correlating said speed data to said event data.

16. A method for collecting and analyzing ambient condition information comprising the steps of:

collecting a plurality of speed data points for a plurality of vehicles operating in a geographic area according to a plurality of dispatch plans identifying a plurality of scheduled stops wherein said speed data includes both vehicle speed and vehicle location;

collecting a plurality of air quality data points for said plurality of vehicles wherein said air quality data points include the concentration of at least one pollutant and vehicle location;

transmitting said speed data points and said air quality data points to a central computer;

segregating a subset of said plurality of speed data points by filtering out speed data points collected when said vehicle is within a predetermined distance from said scheduled stops;

associating said subset of speed data points and said air quality data points with a digital map of said geographic area; and disseminating results of said associating step.

17. The method of claim 16, wherein said step of associating includes determining an average vehicle speed of at least one of said vehicles along at least one road using said subset of speed data points.

18. The method of claim 16, wherein said speed data points and said air quality data points include a time stamp.

19. The method of claim 18, wherein said step of associating includes determining the time taken by at least one vehicle to travel from a first location to a second location proximate a landmark identified on said digital map by subtracting a second time stamp associated with said second location from a first time stamp associated with said first location.

20. The method of claim 16, wherein said subset of speed data points are correlated with said air quality data points at least partially based on said vehicle location.

21. The method of claim 16, wherein said step of disseminating comprises pushing said data to a mobile communication device.

22. A system for collecting ambient condition information for a geographic area comprising:

a plurality of vehicles performing tasks other than data collection in a geographic area according to a dispatch plan;

a plurality air quality monitoring devices installed in said plurality of vehicles configured to collect air quality data including the concentration of at least one pollutant and the physical location of an associated vehicle;

a plurality of speed monitoring devices installed in said plurality of vehicles configured to collect a plurality of speed data points related to the speed of their associated vehicle and the physical location of their associated vehicle;

each of said vehicles including one or more data radios for communicating said air quality data and said speed data; and a central computer configured to receive and analyze said air quality data and said speed data from said one or more data radios and further configured to filter out speed data points collected based in part on said dispatch plan.

23. The system of claim 22, wherein said central computer is configured to segregate speed data and air quality data based on a geographic boundary.

24. The system of claim 22, wherein said central computer is further configured to disseminate the results of said analysis to a plurality of mobile communication devices such that recipients can alter their behavior based in part on said results.

25. A system for collecting meteorological data for a geographic area comprising:

a plurality of vehicles performing tasks other than data collection in a geographic area according to a dispatch plan;

a plurality of speed monitoring devices installed in said plurality of vehicles configured to collect a plurality of speed data points related to the speed of their respective vehicle and the physical location of their respective vehicle;

a plurality meteorological sensors installed in said plurality of vehicles configured to collect meteorological data including the physical location of an associated vehicle;

each of said vehicles including one or more data radios for communicating said meteorological data; and a central computer configured to receive and analyze said meteorological data and said speed data points from said one or more data radios and further configured to filter out speed data points collected based in part on said dispatch plan.

26. The system of claim 25, wherein said central computer is further configured to disseminate the results of said analysis to a plurality of mobile communication devices such that recipients can alter their behavior based in part on said results.

27. The system of claim 25, further comprising a telematics device configured to detect when a vehicle's windshield wipers are activated and wherein said central computer is configured to receive a signal indicating said windshield wipers are activated.

* * * * *